US012605140B2

(12) United States Patent
Peterson et al.

(10) Patent No.: US 12,605,140 B2
(45) Date of Patent: Apr. 21, 2026

(54) SYSTEM AND METHOD FOR A VESSEL ASSESSMENT TOOL

(71) Applicant: Bard Access Systems, Inc., Salt Lake City, UT (US)

(72) Inventors: Bart Peterson, Farmington, UT (US); Bradley M. Wilkinson, North Haledon, NJ (US); Kelly E. Harper, West Valley City, UT (US); Tab Robbins, Layton, UT (US); Matthew J. Prince, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 387 days.

(21) Appl. No.: 17/707,662

(22) Filed: Mar. 29, 2022

(65) Prior Publication Data

US 2022/0304652 A1     Sep. 29, 2022

Related U.S. Application Data

(60) Provisional application No. 63/167,219, filed on Mar. 29, 2021.

(51) Int. Cl.
*A61B 8/08*          (2006.01)
*A61B 8/00*          (2006.01)
(52) U.S. Cl.
CPC ............ *A61B 8/0891* (2013.01); *A61B 8/463* (2013.01); *A61B 8/465* (2013.01)
(58) Field of Classification Search
None
See application file for complete search history.

(56) References Cited

U.S. PATENT DOCUMENTS

| | | | |
|---|---|---|---|
| 5,325,293 A | 6/1994 | Dorne | |
| 5,549,554 A | 8/1996 | Miraki | |

(Continued)

FOREIGN PATENT DOCUMENTS

| | | |
|---|---|---|
| CN | 101854853 A | 10/2010 |
| CN | 105054962 A | 11/2015 |

(Continued)

OTHER PUBLICATIONS

Beigi, P. et al., "Enhancement of needle visualization and localization in ultrasound." International Journal of Computer Assisted Radiology and Surgery, vol. 16, No. 130, Sep. 2020 [Sep. 30, 2020] pp. 169-178.

(Continued)

*Primary Examiner* — Jonathan Cwern
(74) *Attorney, Agent, or Firm* — Rutan & Tucker LLP

(57) ABSTRACT

Embodiments disclosed herein are directed to a vessel assessment system configured to image a target vessel and determine which vascular access device (VAD) to use to access the target vessel while remaining within one or more insertion parameters of percentage vessel occupancy, and dwell length given a predetermined range of insertion angles. The system can superimpose a target vessel sizing ring to measure a diameter or cross-sectional area, or to measure a depth of the target vessel. Further, the system can provide a list of VAD's that can access the target vessel within one or more insertion parameters. The system can provide an icon representing the VAD superimposed over the target vessel to provide a visual representation of the vascular access device within the target vessel.

27 Claims, 6 Drawing Sheets

(56)  References Cited

U.S. PATENT DOCUMENTS

| | | | |
|---|---|---|---|
| 5,573,529 A | 11/1996 | Haak et al. | |
| 5,908,387 A | 6/1999 | LeFree et al. | |
| 5,970,119 A | 10/1999 | Hofmann | |
| 5,997,497 A | 12/1999 | Nita et al. | |
| 6,012,034 A | 1/2000 | Hamparian et al. | |
| 6,074,367 A | 6/2000 | Hubbell | |
| 6,543,642 B1 | 4/2003 | Milliorn | |
| 6,554,771 B1 | 4/2003 | Buil et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,687,386 B1 | 2/2004 | Ito et al. | |
| 6,702,749 B2 | 3/2004 | Paladini et al. | |
| 6,754,608 B2 | 6/2004 | Svanerudh et al. | |
| 6,840,379 B2 | 1/2005 | Franks-Farah et al. | |
| 6,857,196 B2 | 2/2005 | Dalrymple | |
| 7,831,449 B2 | 11/2010 | Ying et al. | |
| 9,521,961 B2 | 12/2016 | Silverstein et al. | |
| 9,756,766 B2 | 9/2017 | Best | |
| 9,949,720 B2 | 4/2018 | Southard et al. | |
| 9,950,139 B2 | 4/2018 | Blanchard et al. | |
| 10,849,689 B1 | 12/2020 | Hu et al. | |
| 11,462,324 B1 | 10/2022 | Roh et al. | |
| 11,844,656 B2 | 12/2023 | Urabe et al. | |
| 11,896,425 B2 | 2/2024 | Dhatt et al. | |
| 11,974,813 B1 | 5/2024 | Donhowe et al. | |
| 2003/0028112 A1 | 2/2003 | Paladini et al. | |
| 2003/0047126 A1 | 3/2003 | Tomaschko | |
| 2003/0106825 A1 | 6/2003 | Molina et al. | |
| 2003/0120154 A1 | 6/2003 | Sauer et al. | |
| 2003/0120155 A1 | 6/2003 | Sauer et al. | |
| 2003/0199765 A1 | 10/2003 | Stetten et al. | |
| 2004/0055925 A1 | 3/2004 | Franks-Farah et al. | |
| 2005/0000975 A1 | 1/2005 | Carco et al. | |
| 2005/0165299 A1 | 7/2005 | Kressy et al. | |
| 2006/0004290 A1 | 1/2006 | Smith et al. | |
| 2006/0015039 A1 | 1/2006 | Cassidy et al. | |
| 2006/0020256 A1 | 1/2006 | Bell et al. | |
| 2007/0043341 A1 | 2/2007 | Anderson et al. | |
| 2007/0073155 A1 | 3/2007 | Park et al. | |
| 2007/0199848 A1 | 8/2007 | Ellswood et al. | |
| 2007/0239120 A1 | 10/2007 | Brock et al. | |
| 2007/0249911 A1 | 10/2007 | Simon | |
| 2007/0260213 A1 | 11/2007 | Williams et al. | |
| 2008/0009747 A1 | 1/2008 | Saadat et al. | |
| 2008/0033293 A1 | 2/2008 | Beasley et al. | |
| 2008/0033759 A1 | 2/2008 | Finlay | |
| 2008/0051657 A1 | 2/2008 | Rold | |
| 2008/0058963 A1 | 3/2008 | Garibaldi et al. | |
| 2008/0161687 A1 | 7/2008 | Suri et al. | |
| 2008/0177186 A1 | 7/2008 | Slater et al. | |
| 2008/0218743 A1 | 9/2008 | Stetten et al. | |
| 2008/0300491 A1 | 12/2008 | Bonde et al. | |
| 2009/0143672 A1 | 6/2009 | Harms et al. | |
| 2009/0143684 A1 | 6/2009 | Cermak et al. | |
| 2009/0156926 A1 | 6/2009 | Messerly et al. | |
| 2009/0182224 A1 | 7/2009 | Shmarak et al. | |
| 2009/0221908 A1 | 9/2009 | Glossop | |
| 2009/0234328 A1 | 9/2009 | Cox et al. | |
| 2009/0306509 A1 | 12/2009 | Pedersen et al. | |
| 2010/0080427 A1 | 4/2010 | Yeluri et al. | |
| 2010/0106015 A1 | 4/2010 | Norris | |
| 2010/0106056 A1 | 4/2010 | Norris | |
| 2010/0211026 A2 | 8/2010 | Sheetz et al. | |
| 2010/0305442 A1 | 12/2010 | Tierney et al. | |
| 2010/0312121 A1 | 12/2010 | Guan | |
| 2011/0002884 A1 | 1/2011 | McCauley et al. | |
| 2011/0071404 A1 | 3/2011 | Schmitt et al. | |
| 2011/0166451 A1 | 7/2011 | Blaivas et al. | |
| 2011/0245659 A1 | 10/2011 | Ma et al. | |
| 2011/0295108 A1 | 12/2011 | Cox et al. | |
| 2011/0313293 A1 | 12/2011 | Lindekugel et al. | |
| 2012/0078103 A1 | 3/2012 | Tashiro et al. | |
| 2012/0143029 A1 | 6/2012 | Silverstein et al. | |
| 2012/0165679 A1 | 6/2012 | Orome et al. | |
| 2012/0197132 A1 | 8/2012 | O'Connor | |
| 2012/0253200 A1 | 10/2012 | Stolka et al. | |
| 2013/0006102 A1 | 1/2013 | Wilkes et al. | |
| 2013/0102889 A1* | 4/2013 | Southard | C08G 61/125 |
| | | | 600/424 |
| 2013/0131499 A1 | 5/2013 | Chan et al. | |
| 2013/0218024 A1 | 8/2013 | Boctor et al. | |
| 2013/0261553 A1 | 10/2013 | Sheldon et al. | |
| 2014/0155744 A1 | 6/2014 | Pameijer | |
| 2014/0275997 A1 | 9/2014 | Chopra et al. | |
| 2014/0287393 A1 | 9/2014 | Kumar et al. | |
| 2014/0303423 A1 | 10/2014 | Amthor et al. | |
| 2014/0343406 A1 | 11/2014 | Damjanovic | |
| 2015/0148668 A1 | 5/2015 | Stolka et al. | |
| 2015/0182144 A1 | 7/2015 | Bharat et al. | |
| 2015/0216442 A1 | 8/2015 | Lavy et al. | |
| 2015/0250437 A1 | 9/2015 | Zaiki | |
| 2015/0272553 A1 | 10/2015 | Thattari Kandiyil et al. | |
| 2015/0320325 A1 | 11/2015 | Sheehan et al. | |
| 2015/0320481 A1 | 11/2015 | Cosman, Jr. et al. | |
| 2015/0359991 A1 | 12/2015 | Dunbar et al. | |
| 2016/0051224 A1 | 2/2016 | Striano | |
| 2016/0128719 A1 | 5/2016 | Cermak | |
| 2016/0174937 A1 | 6/2016 | Bakshi et al. | |
| 2016/0213398 A1 | 7/2016 | Liu | |
| 2016/0300120 A1 | 10/2016 | Haas et al. | |
| 2016/0302772 A1 | 10/2016 | Cummins et al. | |
| 2016/0331469 A1 | 11/2016 | Hall et al. | |
| 2016/0374644 A1 | 12/2016 | Mauldin, Jr. et al. | |
| 2017/0035514 A1 | 2/2017 | Fox et al. | |
| 2017/0056062 A1 | 3/2017 | Buljubasic | |
| 2017/0079551 A1 | 3/2017 | Henkel et al. | |
| 2017/0188990 A1 | 7/2017 | Von Allmen et al. | |
| 2017/0245831 A1 | 8/2017 | Nishigaki et al. | |
| 2017/0265946 A1 | 9/2017 | Ramachandran et al. | |
| 2017/0290563 A1 | 10/2017 | Cole et al. | |
| 2018/0015256 A1* | 1/2018 | Southard | A61B 8/0841 |
| 2018/0036084 A1 | 2/2018 | Krimsky | |
| 2018/0061546 A1 | 3/2018 | Ma et al. | |
| 2018/0125450 A1 | 5/2018 | Blackbourne et al. | |
| 2018/0132944 A1 | 5/2018 | Yan et al. | |
| 2018/0228465 A1 | 8/2018 | Southard et al. | |
| 2018/0289929 A1 | 10/2018 | Ma et al. | |
| 2018/0310955 A1 | 11/2018 | Lindekugel et al. | |
| 2019/0000478 A1 | 1/2019 | Messerly et al. | |
| 2019/0026438 A1 | 1/2019 | Ma et al. | |
| 2019/0105017 A1 | 4/2019 | Hastings | |
| 2019/0282262 A1 | 9/2019 | Bouazza-Marouf et al. | |
| 2019/0298278 A1 | 10/2019 | Nachabe et al. | |
| 2019/0374290 A1 | 12/2019 | Stolka et al. | |
| 2020/0090331 A1 | 3/2020 | Mansi et al. | |
| 2020/0113540 A1 | 4/2020 | Gijsbers et al. | |
| 2020/0219258 A1 | 7/2020 | Saget et al. | |
| 2020/0230391 A1 | 7/2020 | Burkholz et al. | |
| 2020/0234812 A1 | 7/2020 | Willybiro et al. | |
| 2020/0237403 A1 | 7/2020 | Southard et al. | |
| 2020/0245969 A1 | 8/2020 | Tung et al. | |
| 2020/0275949 A1 | 9/2020 | Masotti et al. | |
| 2020/0297235 A1 | 9/2020 | Sanchez et al. | |
| 2020/0315592 A1 | 10/2020 | Soleimani et al. | |
| 2020/0359990 A1 | 11/2020 | Poland et al. | |
| 2020/0397399 A1 | 12/2020 | Adams et al. | |
| 2021/0015448 A1 | 1/2021 | Sokulin et al. | |
| 2021/0045717 A1 | 2/2021 | Schwab | |
| 2021/0059636 A1 | 3/2021 | Durfee et al. | |
| 2021/0085282 A1 | 3/2021 | Prince | |
| 2021/0138130 A1 | 5/2021 | Kotanko et al. | |
| 2021/0169585 A1 | 6/2021 | Prince et al. | |
| 2021/0186456 A1 | 6/2021 | Prince | |
| 2021/0186467 A1 | 6/2021 | Urabe et al. | |
| 2021/0201080 A1 | 7/2021 | Kitahara | |
| 2021/0275256 A1 | 9/2021 | Sowards et al. | |
| 2021/0315542 A1 | 10/2021 | Oura et al. | |
| 2021/0322106 A1 | 10/2021 | Mo et al. | |
| 2022/0013218 A1 | 1/2022 | Cousin | |
| 2022/0022969 A1 | 1/2022 | Misener | |
| 2022/0027257 A1 | 1/2022 | Harutyunyan et al. | |
| 2022/0039685 A1 | 2/2022 | Misener et al. | |

(56)                References Cited

U.S. PATENT DOCUMENTS

| | | | |
|---|---|---|---|
| 2022/0054869 A1 | 2/2022 | Stein et al. |
| 2022/0096797 A1 | 3/2022 | Prince |
| 2022/0101980 A1 | 3/2022 | Rothenberg et al. |
| 2022/0104886 A1 | 4/2022 | Blanchard et al. |
| 2022/0117582 A1 | 4/2022 | McLaughlin et al. |
| 2022/0142608 A1 | 5/2022 | Matsumoto |
| 2022/0160434 A1 | 5/2022 | Messerly et al. |
| 2022/0189610 A1 | 6/2022 | Long et al. |
| 2022/0230714 A1 | 7/2022 | Batman et al. |
| 2022/0241014 A1 | 8/2022 | Kleyman et al. |
| 2022/0280246 A1 | 9/2022 | Messerly et al. |
| 2022/0392642 A1 | 12/2022 | Dasi et al. |
| 2022/0401157 A1 | 12/2022 | Sowards et al. |
| 2022/0406460 A1 | 12/2022 | Golan et al. |
| 2023/0030941 A1 | 2/2023 | Han |
| 2023/0121370 A1 | 4/2023 | Sowards et al. |
| 2023/0147164 A1 | 5/2023 | Sowards et al. |
| 2023/0148993 A1 | 5/2023 | Sowards et al. |
| 2023/0225702 A1 | 7/2023 | Sakalauskas |
| 2023/0260107 A1 | 8/2023 | Dhatt et al. |
| 2023/0329748 A1 | 10/2023 | Sowards et al. |
| 2023/0338003 A1 | 10/2023 | Misener et al. |
| 2023/0380906 A1 | 11/2023 | Misener et al. |
| 2023/0404683 A1 | 12/2023 | Schmidt et al. |
| 2023/0420105 A1 | 12/2023 | Misener et al. |
| 2024/0008894 A1 | 1/2024 | Sowards et al. |
| 2024/0156429 A1 | 5/2024 | Dhatt et al. |
| 2024/0245386 A1 | 7/2024 | Prince |
| 2024/0249831 A1 | 7/2024 | Jesneck et al. |
| 2024/0274297 A1 | 8/2024 | Sillesen et al. |
| 2024/0390605 A1 | 11/2024 | Burkholz et al. |
| 2024/0416077 A1 | 12/2024 | Andersen et al. |
| 2025/0000585 A1 | 1/2025 | Sinha et al. |
| 2025/0255576 A1 | 8/2025 | Prince |

FOREIGN PATENT DOCUMENTS

| | | | |
|---|---|---|---|
| CN | 216167530 U | 4/2022 |
| EP | 1504713 A1 | 2/2005 |
| EP | 0788329 B1 | 12/2006 |
| JP | 2018175547 A | 11/2018 |
| KR | 20180070878 A | 6/2018 |
| WO | 2013059714 A1 | 4/2013 |
| WO | 2014053934 A1 | 4/2014 |
| WO | 2015/017270 A1 | 2/2015 |
| WO | 2018/026878 A1 | 2/2018 |
| WO | 2019/232451 A1 | 12/2019 |
| WO | 2020/002620 A1 | 1/2020 |
| WO | 2020150501 A1 | 7/2020 |
| WO | 2020160550 A1 | 8/2020 |
| WO | 2020/186198 A1 | 9/2020 |
| WO | 2021113733 A1 | 6/2021 |
| WO | 2022/067101 A1 | 3/2022 |
| WO | 2022/072727 A2 | 4/2022 |
| WO | 2022/081904 A1 | 4/2022 |
| WO | 2022150411 A1 | 7/2022 |
| WO | 2022/187701 A1 | 9/2022 |
| WO | 2022212414 A1 | 10/2022 |
| WO | 2022271728 A1 | 12/2022 |
| WO | 2023064492 A1 | 4/2023 |
| WO | 2023081414 A1 | 5/2023 |
| WO | 2023091427 A1 | 5/2023 |
| WO | 2023205019 A1 | 10/2023 |
| WO | 2023205052 A1 | 10/2023 |
| WO | 2023230284 A1 | 11/2023 |
| WO | 2023244640 A1 | 12/2023 |
| WO | 2023250001 A1 | 12/2023 |
| WO | 2024010874 A1 | 1/2024 |

OTHER PUBLICATIONS

PCT/US2023/018340 filed Apr. 12, 2023 International Seach Report and Written Opinion dated Jul. 20, 2023.

PCT/US2023/018680 filed Apr. 14, 2023 International Seach Report and Written Opinion dated Aug. 11, 2013.

PCT/US2023/023616 filed May 25, 2023 International Search Report and Written Opinion dated Aug. 16, 2023.

U.S. Appl. No. 17/725,370, filed Apr. 20, 2022 Non-Final Office Action dated Aug. 4, 2023.

PCT/US2022/046606 filed Oct. 13, 2022 International Search Report and Written Opinion dated Feb. 6, 2023.

PCT/US2022/049042 filed Nov. 4, 2022 International Search Report and Written Opinion dated Mar. 1, 2023.

PCT/US2022/049989 filed Nov. 15, 2022 International Search Report and Written Opinion dated Feb. 6, 2023.

U.S. Appl. No. 17/112,725, filed Dec. 4, 2020 Final Office Action dated Apr. 14, 2023.

U.S. Appl. No. 17/485,035, filed Sep. 24, 2021 Non-Final Office Action dated May 3, 2023.

U.S. Appl. No. 17/725,370, filed Apr. 20, 2022 Restriction Requirement dated Apr. 27, 2023.

PCT/US2022/022400 filed Mar. 29, 2022 International Search Report and Written Opinion dated Jul. 8, 2022.

PCT/US2022/034380 filed Jun. 21, 2022 International Search Report and Written Opinion dated Oct. 5, 2022.

U.S. Appl. No. 17/112,735, filed Dec. 4, 2022 Non-Final Office Action dated Oct. 26, 2022.

Murphy, Ethan K., et al., "Phantom Studies of Fused-Data TREIT Using Only Biopsy-Probe Electrodes" IEEE Transactions On Medical Imaging, IEEE, USA. vol. 39 No. 114, May 2020. (May 4, 2020).

PCT/US2012/061182 International Seach Report and Written Opinion dated Mar. 11, 2013.

PCT/US2020/063441 filed Dec. 4, 2020 International Preliminary Report on Patentability dated May 17, 2022.

PCT/US2020/063441 filed Dec. 4, 2020 International Search Report and Written Opinion dated Mar. 19, 2021.

PCT/US2021/052055 filed Sep. 24, 2021 International Search Report and Written Opinion dated Dec. 20, 2021.

PCT/US2022/019017 filed Mar. 4, 2022 International Search Report and Written Opinion dated Jun. 14, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

U.S. Appl. No. 13/656,563, filed Oct. 19, 2012 Decision on Appeal dated Nov. 1, 2017.

U.S. Appl. No. 13/656,563, filed Oct. 19, 2012 Examiner's Answer dated Nov. 16, 2015.

U.S. Appl. No. 13/656,563, filed Oct. 19, 2012 Final Office Action dated Dec. 5, 2014.

U.S. Appl. No. 13/656,563, filed Oct. 19, 2012 Non-Final Office Action dated Jul. 18, 2014.

U.S. Appl. No. 15/951,903, filed Apr. 12, 2018 Advisory Action dated Dec. 22, 2020.

U.S. Appl. No. 15/951,903, filed Apr. 12, 2018 Board Decision dated Apr. 20, 2022.

U.S. Appl. No. 15/951,903, filed Apr. 12, 2018 Examiner's Answer dated Jun. 3, 2021.

U.S. Appl. No. 15/951,903, filed Apr. 12, 2018 Final Office Action dated Oct. 13, 2020.

U.S. Appl. No. 15/951,903, filed Apr. 12, 2018 Non-Final Office Action dated May 22, 2020.

U.S. Appl. No. 15/951,903, filed Apr. 12, 2018 Notice of Allowance dated May 2, 2022.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

U.S. Appl. No. 17/725,370, filed Apr. 20, 2022 Final Office Action dated Feb. 15, 2024.

PCT/US2023/025259 filed Jun. 14, 2023 International Search Report and Written Opinion dated Sep. 25, 2023.

PCT/US2023/025845 filed Jun. 21, 2023 International Search Report and Written Opinion dated Sep. 26, 2023.

(56)                    References Cited

OTHER PUBLICATIONS

PCT/US2023/027042 filed Jul. 6, 2023 International Search Report and Written Opinion dated Oct. 10, 2023.
Schmidt G A et al Ultrasound-guided 1-22 vascular access in critical illness Intensive Care Medicine Springer Berlin Heidelberg Berlin/Heidelberg vol. 45 No. 4 Feb. 18, 2019 Feb. 18, 2019 pp. 434-446 XP036747615 ISSN 0342-4642 DOI 10.1007/S00134-019-05564-7 retrieved on 2019-02-181.
U.S. Appl. No. 17/485,035, filed Sep. 24, 2021 Notice of Allowance dated Nov. 8, 2023.
U.S. Appl. No. 17/825,976, filed May 26, 2022 Non-Final Office Action dated Aug. 5, 2025.
U.S. Appl. No. 17/841,541, filed Jun. 15, 2022 Final Office Action dated Jul. 23, 2025.
U.S. Appl. No. 17/849,455, filed Jun. 24, 2022 Advisory Action dated Jul. 11, 2025.
U.S. Appl. No. 17/849,455, filed Jun. 24, 2022 Non-Final Office Action dated Sep. 5, 2025.
U.S. Appl. No. 17/965,657, filed Oct. 13, 2022 Notice of Allowance dated Sep. 24, 2025.
U.S. Appl. No. 17/981,313, filed Nov. 4, 2022 Non-Final Office Action dated Jul. 22, 2025.
U.S. Appl. No. 17/987,717, filed Nov. 15, 2022 Notice of Allowance dated Jul. 15, 2025.
U.S. Appl. No. 17/687,476, filed Mar. 4, 2022 Notice of Allowance dated Mar. 5, 2025.
U.S. Appl. No. 17/724,371, filed Apr. 19, 2022 Final Office Action dated Mar. 7, 2025.
U.S. Appl. No. 17/825,976, filed May 26, 2022 Final Office Action dated Mar. 25, 2025.
U.S. Appl. No. 17/841,541, filed Jun. 15, 2022 Non-Final Office Action dated Mar. 14, 2025.
U.S. Appl. No. 17/845,818, filed Jun. 21, 2022 Restriction Requirement dated Feb. 10, 2025.
U.S. Appl. No. 17/849,455, filed Jun. 24, 2022 Non-Final Office Action dated Jan. 24, 2025.
U.S. Appl. No. 17/859,980, filed Jul. 7, 2022 Advisory Action dated Feb. 10, 2025.
U.S. Appl. No. 17/965,657, filed Oct. 13, 2022 Non-Final Office Action dated Jan. 6, 2025.
U.S. Appl. No. 17/987,717, filed Nov. 15, 2022 Non-Final Office Action dated Mar. 21, 2025.
U.S. Appl. No. 18/601,980, filed Mar. 11, 2024 Notice of Allowance dated Jan. 10, 2025.
U.S. Appl. No. 17/687,476, filed Mar. 4, 2022 Non-Final Office Action dated Nov. 1, 2024.
U.S. Appl. No. 17/724,371, filed Apr. 19, 2022 Non-Final Office Action dated Nov. 26, 2024.
U.S. Appl. No. 17/849,455, filed Jun. 24, 2022 Advisory Action dated Dec. 17, 2024.
U.S. Appl. No. 17/849,455, filed Jun. 24, 2022 Final Office Action dated Nov. 7, 2024.
U.S. Appl. No. 17/859,980, filed Jul. 7, 2022 Final Office Action dated Dec. 5, 2024.
U.S. Appl. No. 17/981,313, filed Nov. 4, 2022 Non-Final Office Action dated Oct. 8, 2024.
U.S. Appl. No. 17/724,371, filed Apr. 19, 2022 Advisory Action dated May 14, 2025.
U.S. Appl. No. 17/724,371, filed Apr. 19, 2022 Non-Final Office Action dated Jun. 12, 2025.
U.S. Appl. No. 17/825,976, filed May 26, 2022 Advisory Action dated Jun. 9, 2025.
U.S. Appl. No. 17/845,818, filed Jun. 21, 2022 Non-Final Office Action dated Jun. 17, 2025.
U.S. Appl. No. 17/849,455, filed Jun. 24, 2022 Final Office Action dated May 7, 2025.
U.S. Appl. No. 17/859,980, filed Jul. 7, 2022 Non-Final Office Action dated May 29, 2025.
U.S. Appl. No. 17/965,657, filed Oct. 13, 2022 Final Office Action dated May 22, 2025.
U.S. Appl. No. 17/981,313, filed Nov. 4, 2022 Advisory Action dated Jun. 26, 2025.
U.S. Appl. No. 17/981,313, filed Nov. 4, 2022 Final Office Action dated Apr. 15, 2025.
U.S. Appl. No. 17/724,371, filed Apr. 19, 2022 Advisory Action dated Sep. 20, 2024.
U.S. Appl. No. 17/724,371, filed Apr. 19, 2022 Final Office Action dated Jul. 24, 2024.
U.S. Appl. No. 17/725,370, filed Apr. 20, 2022 Notice of Allowance dated Sep. 18, 2024.
U.S. Appl. No. 17/849,455, filed Jun. 24, 2022 Non-Final Office Action dated Jul. 18, 2024.
U.S. Appl. No. 18/601,980, filed Mar. 11, 2024 Non-Final Office Action dated Sep. 27, 2024.
U.S. Appl. No. 17/724,371, filed Apr. 19, 2022 Non-Final Office Action dated Apr. 12, 2024.
U.S. Appl. No. 17/825,976, filed May 26, 2022 Restriction Requirement dated Apr. 12, 2024.
U.S. Appl. No. 17/859,980, filed Jul. 7, 2022 Non-Final Office Action dated Jul. 1, 2024.
U.S. Appl. No. 17/724,371, filed Apr. 19, 2022 Final Office Action dated Oct. 29, 2025.
U.S. Appl. No. 17/841,541, filed Jun. 15, 2022 Non-Final Office Action dated Dec. 1, 2025.
U.S. Appl. No. 17/845,818, filed Jun. 21, 2022 Notice of Allowance dated Oct. 28, 2025.
U.S. Appl. No. 17/849,455, filed Jun. 24, 2022 Final Office Action dated Dec. 29, 2025.
U.S. Appl. No. 17/859,980, filed Jul. 7, 2022 Final Office Action dated Oct. 16, 2025.
U.S. Appl. No. 17/724,371, filed Apr. 19, 2022 Advisory Action dated Jan. 9, 2026.
U.S. Appl. No. 17/825,976, filed May 26, 2022 Final Office Action dated Feb. 5, 2026.
U.S. Appl. No. 17/981,313, filed Nov. 4, 2022 Final Office Action dated Jan. 27, 2026.

* cited by examiner

400

402  Imaging target area for one or more target vessels

404  Entering parameters          406  Selecting target vessel

408  Determining selection of catheters

410  Selecting catheter to use

412  Depicting image overlay of selected catheter in target vessel

SYSTEM AND METHOD FOR A VESSEL ASSESSMENT TOOL

PRIORITY

This application claims the benefit of priority to U.S. Provisional Application No. 63/167,219, filed Mar. 29, 2021, which is incorporated by reference in its entirety into this application.

SUMMARY

Embodiments disclosed herein are directed to a system and method for a vessel assessment tool configured to image a target vessel, disposed subcutaneously, and determine which vascular access device to use to access the target vessel, while remaining within one or more predetermined parameters of percentage vessel occupancy, and dwell length given a predetermined range of insertion angles.

When placing a vascular access device ("VAD") such as a catheter, central venous catheter ("CVC"), peripherally inserted central catheter ("PICC"), peripheral intravenous catheter ("PIV"), or the like, clinicians must select a VAD based upon a number of different parameters. Current systems require clinicians to select a particular VAD first and then use various imaging tools to evaluate if the selected VAD is appropriate or not. This necessitates a certain amount of "trial and error" on the part of the clinician to select the correct VAD prior to locating an appropriate vessel to access.

Embodiments described herein are directed to a vessel assessment tool configured to image one or more target vessels of a patient and, according to one or more predetermined parameters, provide one or more VAD tools that are most suited to accessing the vessel.

Disclosed herein is a vessel assessment system including, an ultrasound probe, and a console communicatively coupled to the ultrasound probe, the console including a display and one or more logic modules coupled to one or both of a processor and a data store, the one or more logic modules including, an imaging logic configured to provide an image of a target vessel, a vessel selection logic configured to determine one or both of a diameter and a cross-sectional area of the target vessel, and a VAD selection logic configured to retrieve an insertion parameter, and select a VAD icon from a list of VAD icons, the VAD icon representing a vascular access device configured to access the target vessel within the insertion parameter.

In some embodiments, the ultrasound probe is configured to send an acoustic signal and detect a reflected acoustic signal, and the imaging logic is configured to retrieve information from the ultrasound probe and provide an image of the target vessel disposed subcutaneously.

In some embodiments, the vessel selection logic is configured to retrieve image information from the imaging logic, and automatically align a vessel selection ring, superimposed on the image, with the target vessel.

In some embodiments, the vessel selection logic is configured to receive an input from a user to manipulate a vessel selection ring, superimposed on the image, to align with the target vessel.

In some embodiments, the vessel selection ring can change one or more of a diameter and a shape to align the vessel selection ring with the target vessel.

In some embodiments, the insertion parameter includes one or more of a percentage vessel occupancy parameter, a dwell length parameter, and an insertion angle parameter.

In some embodiments, the VAD selection logic is further configured to superimpose the VAD icon on the image, and align the VAD icon with the target vessel.

In some embodiments, the size of the VAD icon is scaled relative to the target vessel to provide a visual comparison of the vascular access device relative to the target vessel.

In some embodiments, the VAD icon of the list of VAD icons includes a specification measurement of the vascular access device, each VAD icon of the list of one or more VAD icons representing a different vascular access device.

Also disclosed is a vessel assessment tool including, a processor, and memory communicatively coupled to the processor, the memory including machine readable instructions that when executed by the processor, cause the processor to execute, i) an imaging logic configured to provide an image of a target vessel disposed subcutaneously, ii) a vessel selection logic configured to determine one or more of a diameter, a cross-sectional area, and a depth of the target vessel, and iii) a VAD selection logic configured to retrieve information from the vessel selection logic, and retrieve an insertion parameter, and provide a VAD icon representing a vascular access device configured to access the target vessel within the insertion parameter.

In some embodiments, the vessel assessment tool further includes an ultrasound probe configured to send and receive an acoustic signal, and wherein the imaging logic is configured to retrieve information from the ultrasound probe to provide the image of the target vessel.

In some embodiments, the vessel selection logic is further configured to identify one or more features of the image, and automatically align a vessel selection ring, superimposed on the image, with the target vessel.

In some embodiments, the vessel selection logic is further configured to receive an input from a user to manipulate a vessel selection ring, superimposed on the image, to align with the target vessel.

In some embodiments, the vessel selection logic is configured to change one or more of a position, a diameter, an area, and a shape of the vessel selection ring, to align the vessel selection ring with the target vessel.

In some embodiments, the VAD icon is superimposed on the image, and aligned with the target vessel.

In some embodiments, the size of the VAD icon is scaled relative to the image to provide a visual comparison of the vascular access device relative to the target vessel.

In some embodiments, the VAD selection logic provides a list of one or more VAD icons, each VAD icon of the list of one or more VAD icons representing a different vascular access device.

In some embodiments, the VAD selection logic is configured to receive an input to select a second VAD icon from the list of one or more VAD icons, representing a second vascular access device.

Also disclosed is a method of selecting a vascular access device for accessing a target vessel including, detecting a reflected ultrasonic acoustic signal using an ultrasonic imaging device, providing an image of the target vessel disposed subcutaneously, determining one or more of a depth, a diameter, and a cross-sectional area of the target vessel, retrieving an insertion parameter including one or more of a maximum percentage vessel occupancy parameter, a minimum dwell length parameter, and an insertion angle parameter, and automatically selecting, by a VAD selection logic, a vascular access device, a diameter of the vascular access device being equal to or less than the maximum percentage vessel occupancy parameter, or a dwell length metric of the vascular access device being equal to or greater than the minimum dwell length parameter.

In some embodiments, the method further includes the VAD selection logic automatically aligning a vessel selection ring, superimposed on the image, with the target vessel.

In some embodiments, the method further includes providing an input to the VAD selection logic to modify a vessel selection ring, superimposed on the image, to align the vessel selection ring with the target vessel.

In some embodiments, the method further includes retrieving the insertion angle parameter, the depth of the target vessel and a total length of the vascular access device and determining the dwell length metric of the vascular access device.

In some embodiments, the method further includes superimposing a VAD icon on the image of the target vessel, the VAD icon representing one or both of a diameter and a cross-sectional area of the vascular access device relative to the target vessel.

In some embodiments, the method further includes selecting, by a user interface, a second VAD icon representing a second vascular access device, a diameter of the second vascular access device being less than the maximum percentage vessel occupancy parameter, or a dwell length metric of the second vascular access device being greater than the minimum dwell length parameter.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
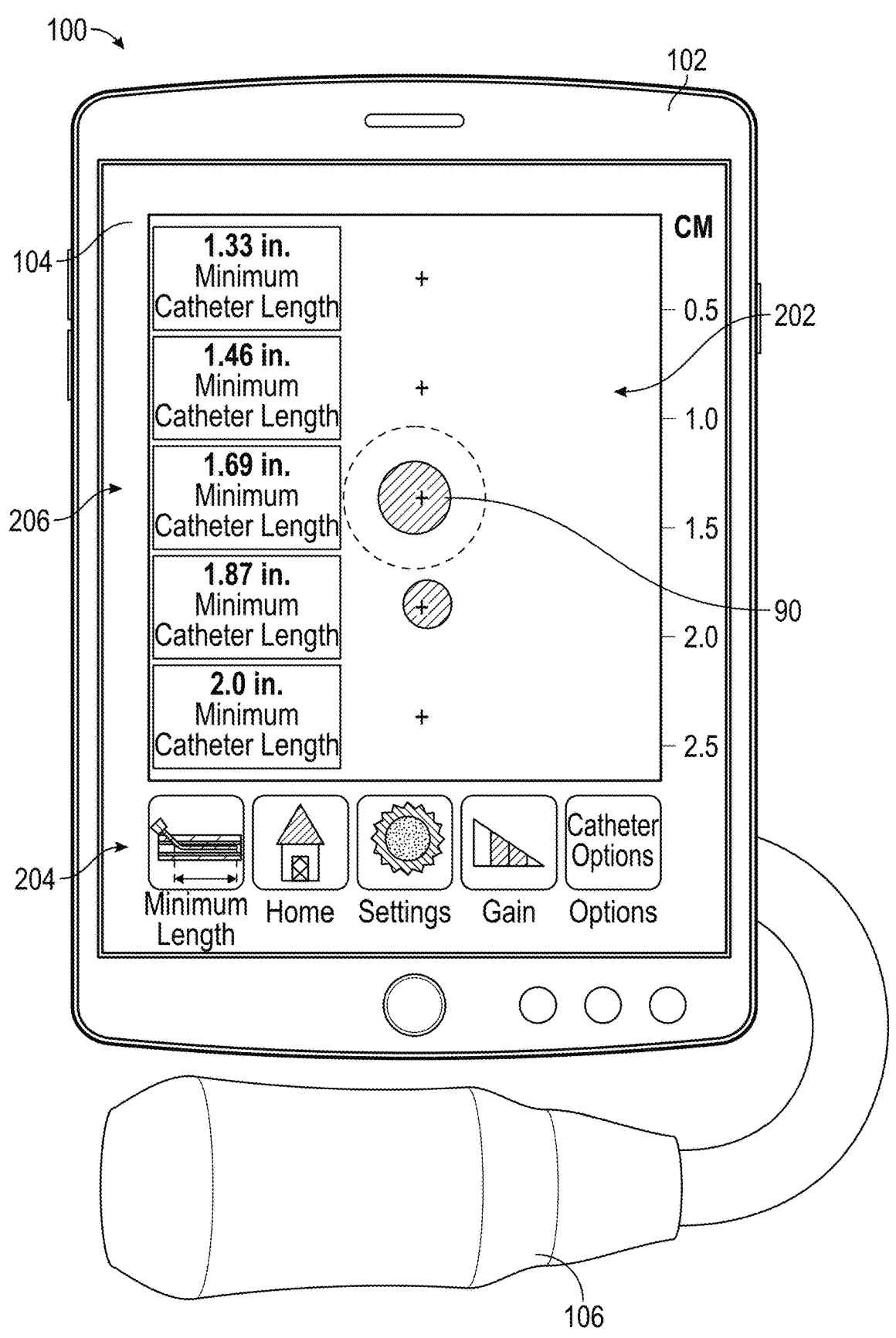
FIG. 1A illustrates an exemplary system configured for targeting a vessel and determining a vascular access device to access the target vessel, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Terminology

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "a first actionable element," may be made. However, the specific numeric reference should not be interpreted as a literal sequential order but rather interpreted that the "first actionable element" is different than a "second actionable element." Thus, the specific details set forth are merely exemplary. The specific details may be varied from and still be contemplated to be within the spirit and scope of the present disclosure. The term "coupled" is defined as meaning connected either directly to the component or indirectly to the component through another component, where the connection may enable communications between these components.

As used herein, the term "communication" generally refers to related data that is received, transmitted, or exchanged within a communication session. The data may include a plurality of packets, where a "packet" broadly refers to a series of bits or bytes having a prescribed format. Alternatively, the data may include a collection of data that may take the form of an individual or a number of packets carrying related payloads, e.g., a single webpage received over a network. Further, as used herein, the terms "about," "approximately," or "substantially" for any numerical values or ranges indicate a suitable dimensional tolerance that allows the part or collection of components to function for its intended purpose as described herein.

In the following description, certain terminology is used to describe features of the invention. For example, in certain situations, the term "logic" is representative of hardware, firmware and/or software that is configured to perform one or more functions. As hardware, logic may include circuitry having data processing or storage functionality. Examples of such circuitry may include, but are not limited or restricted to a microprocessor, one or more processor cores, a programmable gate array, a microcontroller, a controller, an application specific integrated circuit ("ASIC"), wireless receiver, transmitter and/or transceiver circuitry, semiconductor memory, or combinatorial logic.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage. In an embodiment, the logic described herein may rely on heuristics, machine learning, artificial intelligence (A.I.), neural networks, or other data processing techniques to perform the described functionality.

The term "computing device" may be construed as electronics with data processing capabilities and/or a network interface capabilities, such as network connectivity to a physical or virtual network such as a public network (e.g., Internet), a private network (e.g., a wireless data telecommunication network, a local area network "LAN", etc.), a public cloud network, a virtual private cloud, of the like. Examples of a computing device may include, but are not limited or restricted to, the following: a server, an endpoint device (e.g., a laptop, a smartphone, a "wearable" device, a smartwatch, a tablet, a desktop or laptop computer, a netbook, or any general-purpose or special-purpose, user-controlled electronic device); a mainframe; a router; or the like.

The term "network" may include a public and/or private network based on wired or wireless interconnects and in a centralized or decentralized configuration. The networks may include, but are not limited or restricted to a Local Area Network (LAN), a Wireless Local Area Network (WLAN), a Virtual Private Network (VPN), intranet, internet, 'cloud' based network, or similar network configurations.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

As used herein, the term "icon" or "VAD icon" can include any alphanumerical or pictorial symbol to represent a device, e.g. a vascular access device.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition may occur only when a combination of elements, functions, steps or acts are in some way inherently mutually exclusive.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Vessel Assessment Tool

FIG. 1A illustrates an exemplary vessel assessment system ("system") 100 configured to image a subcutaneous target vessel and determine which vascular access device to use to access the target vessel, while remaining within one or more predetermined insertion parameters. Exemplary insertion parameters can include a percentage vessel occupancy, a dwell length, and an insertion angle or insertion angle range. In an embodiment, a vascular access device ("VAD") can include but not limited to, a catheter, dialysis catheter, central venous catheter ("CVC"), peripherally inserted central catheter ("PICC"), peripheral intravenous catheter ("Hy"), midline catheter, sacrificial catheter, introducer, trocar, or the like.

The system 100 can generally include a console 102 including a display 104, and a probe 106 communicatively coupled, either wired or wirelessly, to the console 102. In an embodiment, the system 100 can be configured to image a subcutaneous portion of a patient using one or more modalities. Exemplary modalities can include, but not limited to, electromagnetic, permanent (static) magnetic, optical, acoustic modalities, combinations thereof, or the like. In an embodiment, the system 100 can be configured to use an ultrasound modality to image a target vessel 90 within the patient. In an embodiment, the probe 106 can include a medical device guide (not shown) configured to guide an insertion angle for a VAD within a range of insertion angles.

In an embodiment, the console 100 can include one or more user interface elements 104, such as buttons, keyboards, "mouse", trackpad, trackball, touch screens, voice recognition inputs, combinations thereof, or the like. In an embodiment, the display 104 may be a touch screen and can be included with the console 102. In an embodiment, the display 104 can be a separate stand-alone unit from the console 102 and can be communicatively coupled, either wired or wirelessly, with the console 102. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like.

Figure 1B:
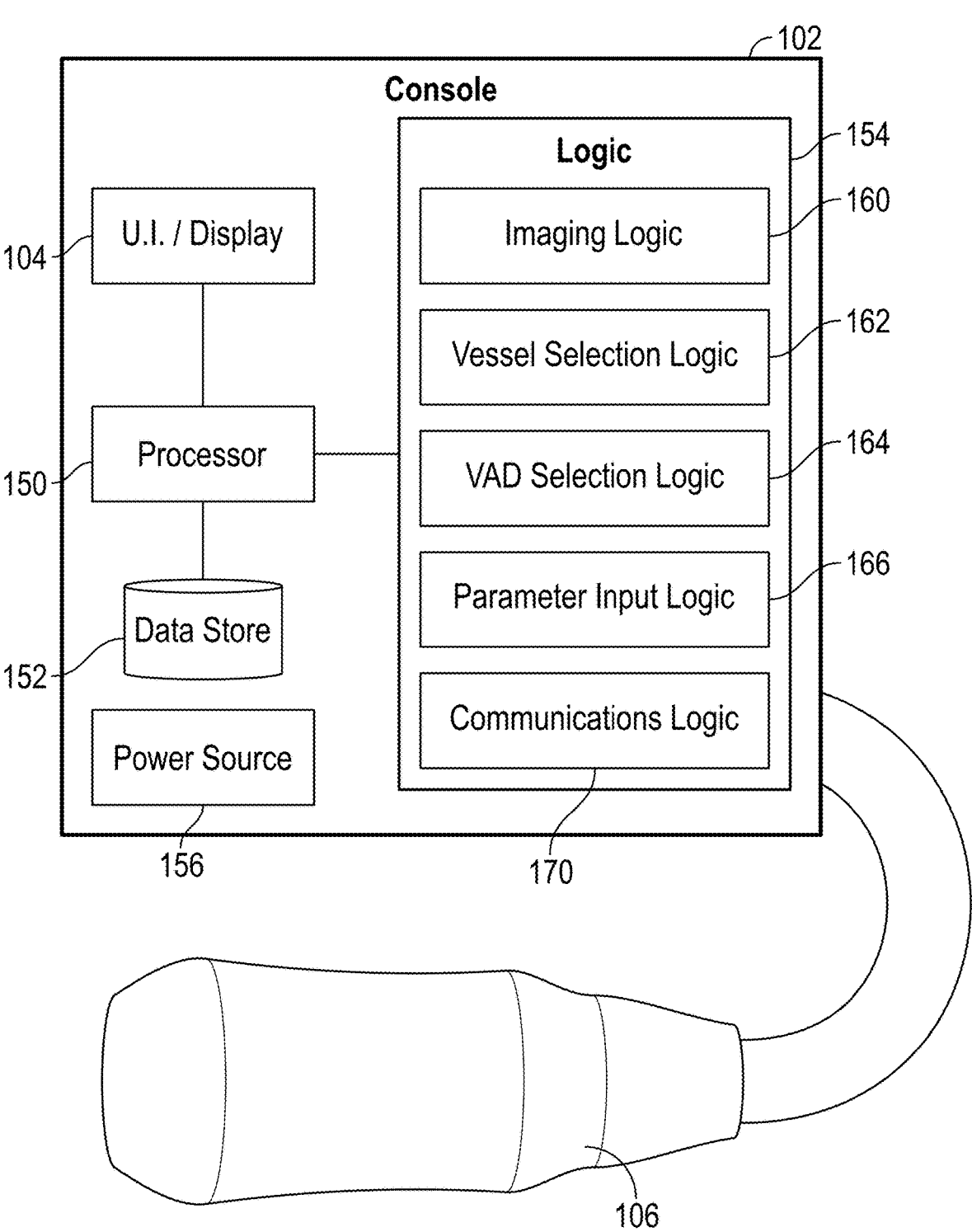
FIG. 1B illustrates a schematic view of the system of FIG. 1A, in accordance with embodiments disclosed herein.

FIG. 1B shows a schematic view of the vessel assessment system 100 of FIG. 1A, the console 102 can include one or more processors 150, data store 152, and one or more logic engines 154, such as an imaging logic 160, a vessel selection logic 162, a VAD selection logic 164, a parameter input logic 166, and a communications logic 170, as described in more detail herein. In an embodiment, the system 100 can further include an internal power source 156 or be powered by a mains power supply.

Figure 2A:
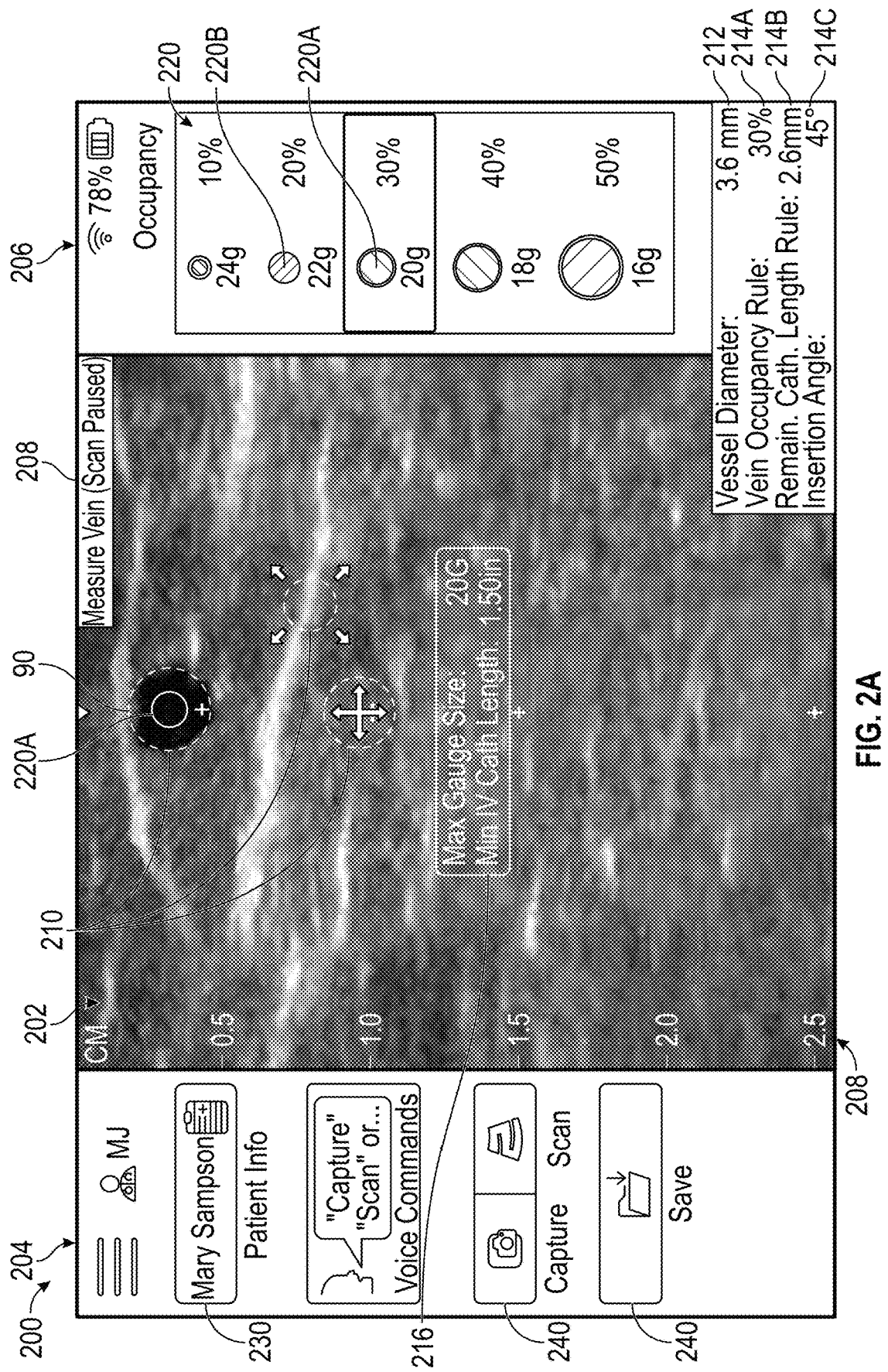
FIG. 2A illustrates a screenshot of the system of FIG. 1A, in accordance with embodiments disclosed herein.

FIG. 2A shows an exemplary screenshot 200 from the display 104 of the system 100. In an embodiment, as shown in FIG. 2A, the screenshot 200 can include an image 202 of a subcutaneous portion of the patient (e.g. an ultrasound image) including a target vessel 90, a user interface section 204, and a VAD selection tool 206.

In an embodiment, the user interface section 204 can display various information about the patient such as name, date of birth, patient ID number, and the like, and/or can include a selection button 230 to display further information about the patient. In an embodiment, the system 100 can provide a patient information interface to allow the clinician to enter or update information about the patient by way of the system 100. In an embodiment, information about the patient can be stored locally, e.g. on data store 152 or can be retrieved from a remote database or network by way of the communications logic 170. Exemplary remote databases or networks can include the internet, hospital intranet, electronic health record (EHR) database, combinations thereof, or the like. In an embodiment, the user interface section 204 can further include one or more image control buttons 240 for manipulating the image 202, e.g. freezing or capturing the image, saving the image to the data store 152, etc. In an embodiment, the system 100 can be controlled by voice recognition commands, the voice recognition commands can be displayed on the user interface section 204.

In an embodiment, the imaging logic 160 can be configured to send and receive signals to/from the probe 106 and the display 104, to provide the image 202 of a subcutaneous portion of the patient. In an embodiment, the imaging logic 160 can be an ultrasound imaging logic configured to send and receive signals to/from an ultrasound probe 106. The ultrasound probe 106 can be configured to emit an ultrasonic acoustic signal and detect a reflected ultrasonic acoustic signal. The ultrasound imaging logic 160 can be configured to display an image of the subcutaneous portion of the patient based on the reflected ultrasonic acoustic signal and can be used to locate a target vessel 90. In an embodiment, the imaging logic 160 can provide image information 208 such as a subcutaneous depth scale, current actions, image scanning or pausing, combinations thereof, or the like. In an embodiment, the imaging logic 160 can provide the image control buttons 240 on the display 104.

In an embodiment, a vessel selection logic 162 can be configured to provide a vessel selection ring 210 superimposed on the image 202. The vessel selection logic 162 can be configured to receive an input from the user to move the vessel selection ring 210 relative to the image 202. In an embodiment, the display 104 is a touch screen display and the user can manipulate the vessel selection ring 210 by touching and dragging across the display 104. However, it will be appreciated that the vessel selection logic 162 can be configured to receive other input(s) from the user to move the vessel selection ring 210 such as keyboards, trackpads, track balls or motion detection devices, voice recognition, combinations thereof, or the like.

In an embodiment, the vessel selection logic 162 can be configured to resize the vessel selection ring 210 to align with one or more of a diameter, size and shape of the target vessel 90. In an embodiment, the vessel selection logic 162 can be configured to change the shape of the vessel selection ring 210 (e.g. circular, elliptical, etc.) to align with the shape of the target vessel 90 and to determine one or more of a minimum diameter, maximum diameter, or cross-sectional area of the target vessel 90. In an embodiment, the vessel selection logic 162 can provide one or more vessel selection rings 210 that can each be aligned with one or more target vessels 90. For example, a first vessel selection ring can be aligned with a first target vessel, a second vessel selection ring can be aligned with a second target vessel, etc.

In an embodiment, the vessel selection logic 162 can be configured to recognize one or more features of the image 202 and automatically align the vessel selection ring 210 with the feature of the image. For example, the vessel selection logic 162 can automatically recognize features within the image that indicate a change in tissue structure. These features can indicate a change in acoustic properties of the tissue that can indicate a boundary of one or more different tissue structures or target vessel(s) 90, etc. As such, the vessel selection logic 162 can the automatically identify one or more target vessels 90 within the image 202 and align and resize the vessel selection ring 210 with a target vessel 90 of the one or more target vessels. In an embodiment, the user can select or further manipulate the vessel selection ring 210 after automatic alignment of the vessel selection ring 210 with the target vessel 90. In an embodiment, the vessel selection logic 162 can be configured to display vessel information 212 on the display 104, for one or more target vessels 90. For example, vessel information 212 can include, but not limited to, a vessel diameter (e.g. minimum, maximum, mean, median diameters), a vessel cross-sectional area, a vessel shape, a depth of the vessel below the skin surface, or the like. The vessel information 212 can be dynamically updated based on position or size of the one or more vessel selection rings 210 in relation to the one or more target vessels 90.

In an embodiment, a VAD selection logic 164 can be configured to retrieve information about the target vessel 90 from the vessel selection logic 162, retrieve information about one or more VAD's, retrieve information about one or more insertion parameters 214, and indicate to the user one or more VAD's that can successfully access the target vessel 90 while remaining within the predetermined insertion parameters 214. As described herein, information about the target vessel 90 can include a diameter, cross-sectional area, a depth of the target vessel 90 relative to a skin surface, a vessel shape (circular or elliptical), combinations thereof, or the like.

Exemplary information about one or more VAD's can include, but not limited to, a make, model, part number, serial number, specifications, diameter, gauge (e.g. 24g, 22g, 20g, 18g, 16g, or the like), a VAD length, a VAD dwell length, a preferred insertion angle or insertion angle range, purchase price, current inventory, ordering information, combinations thereof, or the like. The VAD information can be stored locally on the data store 152, or can be communicated to the system 100 by way of the communications logic 170 from a network or remote database (e.g. an electronic health record database, VAD manufacturer's database, internet, intranet, hospital network, or the like).

As used herein, the insertion parameters 214 can include one or more of a percentage vessel occupancy parameter 214A, a dwell length parameter 214B (either an absolute length metric, or a percentage of total VAD length), and an insertion angle range 214C. However, it will be appreciated that other insertion parameters 214 are also contemplated. The insertion parameters 214 can be entered by a user, derived by the system 100, or can be retrieved from the local data store 152, or retrieved from a network or remote database (e.g. an electronic health record database, VAD manufacturer's database, etc.).

In an embodiment, a percentage vessel occupancy parameter 214A can be a maximum percentage of the diameter or cross-sectional area of the target vessel 90 that is occupied by the VAD, when the VAD is disposed within the target vessel 90. This can be important since a VAD that is larger than a percentage vessel occupancy parameter can occlude the vessel and mitigate blood flow. As a non-limiting example, where a target vessel 90 has a diameter of 3.65 mm and a vessel occupancy parameter is set to 30%, the vessel occupancy logic 164 can determine that (3.65 mm×30%=1.1 mm) or a 20 gauge (20 G) VAD or smaller can be used to access the target vessel 90 while remaining at or below the maximum vessel occupancy parameter.

In an embodiment, a dwell length metric is a length of the VAD that would dwell within target vessel 90, when the VAD accesses the target vessel 90. This can be important since the minimum dwell length metric can ensure that the VAD remains engaged with the vessel throughout the procedure. If the dwell length is too short, then a distal tip of the VAD may be pulled out of the vessel accidentally leading to complications to the patient, aborting the procedure and/or re-accessing the vessel. The dwell length metric can be expressed either as an absolute length, or as a percentage of the total length of the VAD. The dwell length metric can be the length of the VAD disposed within the target vessel 90, given the total length of the VAD. As described in more detail herein, the dwell length of a given VAD can be affected by the depth of the target vessel 90 below the skin surface, and the insertion angle of the VAD.

In an embodiment, the VAD selection logic 164 can be configured to display the VAD selection tool 206 on the display 104. The VAD selection tool 206 can display one or more VAD icons 220 representing one or more VAD's and can include information associated therewith, such as VAD cross-section diameter or gauge, a VAD total length, a percentage vessel occupancy metric or a dwell length metric relative to the target vessel 90, or the like. In an embodiment, an "icon" can include any alphanumerical or pictorial symbol, shape color or graphical representation (e.g. chart, graph, Venn diagram, radar chart, etc.), to represent a device or range of devices. For example, a first VAD icon can represent a first vascular access device or first group of devices, and can differentiate the first VAD icon from a second VAD icon representing a second vascular access device or group of devices. The VAD icon may include one or more specification measurements (length, diameter, gauge, etc.), serial numbers, make, model number, color or any defining information, combinations thereof, or the like, to facilitate differentiating the associated vascular access device or group of devices from a different vascular access device or group of devices. In an embodiment, the VAD icon 220 can be color coded, or include a distinct pattern or symbol to easily differentiate between the different VAD's and associated VAD information. The VAD selection logic 164 can be configured to receive an input from the user to select a first VAD icon 220A, and the VAD selection logic 164 can provide a first VAD icon 220A superimposed on the image 202. In an embodiment, the first VAD icon 220A can be aligned with a center of the target vessel selection ring 210.

In an embodiment the size (e.g. diameter) of the VAD icon 220 can be scaled relative to the image and the size of the target vessel 90. As such, when the VAD icon 220A is superimposed on the image 202, the user can immediately see a size of the VAD relative to the target vessel 90. Advantageously, the size of the VAD icon 220A can allow a user to quickly see if the VAD selection is appropriate. In an embodiment, the VAD selection logic 164 can be configured to provide one or more alerts to indicate to the user if the VAD selected, e.g. the first VAD icon 220A, is within one or more of the insertion parameters 214. Exemplary alerts can be audible, visual or tactile alerts.

Figure 2B:
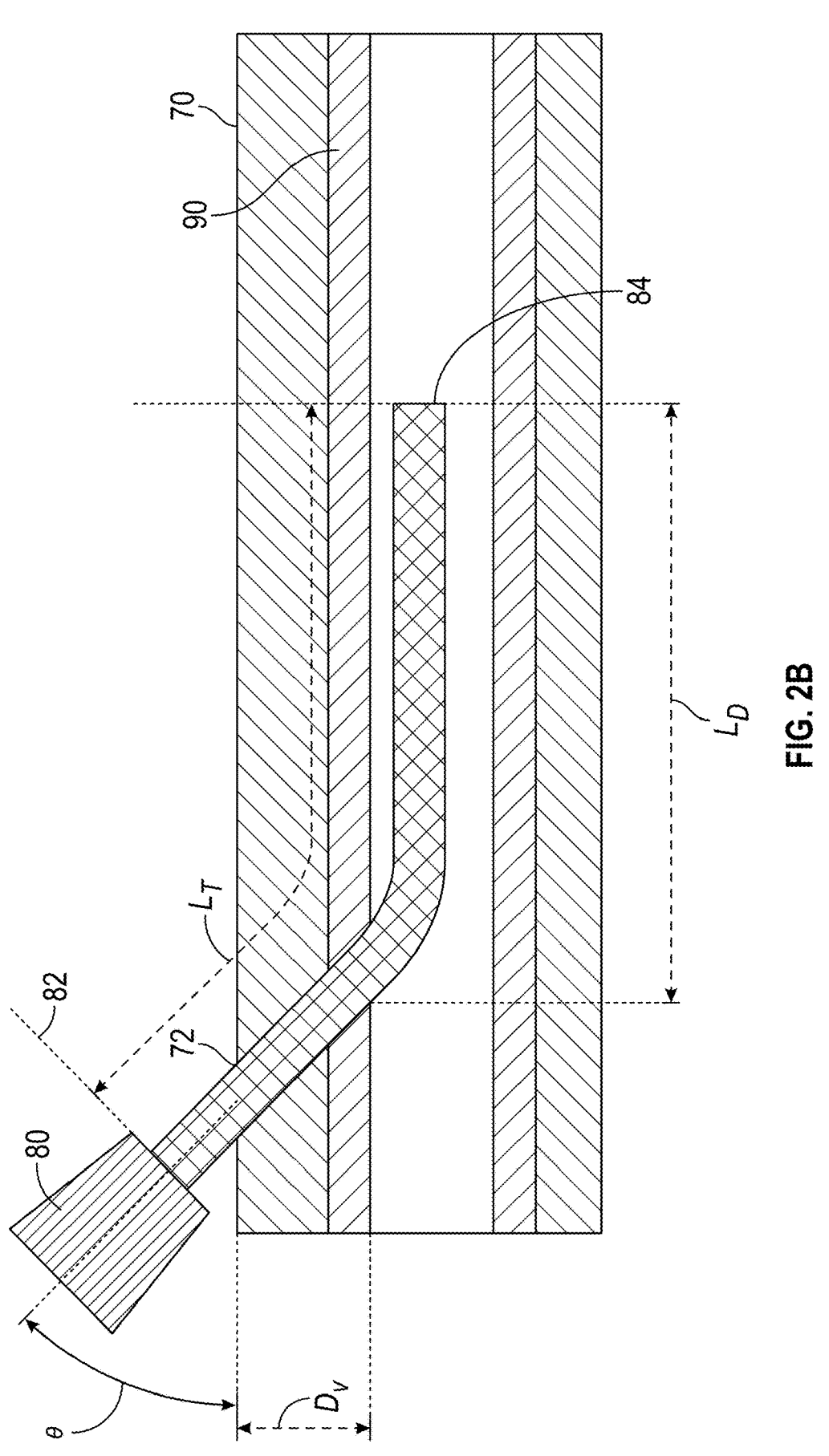
FIG. 2B illustrates a cross-sectional side view of a vascular access device accessing a target vessel, in accordance with embodiments disclosed herein.

In an embodiment, a minimum dwell length parameter can be a minimum longitudinal length of the VAD 80 that is disposed within the target vessel 90 when the VAD accesses the target vessel 90. The minimum dwell length parameter can be expressed either as an absolute length (e.g. in mm or cm), or as a percentage of the total VAD length ($L_T$). FIG. 2B shows a longitudinal cross-sectional view of an exemplary VAD 80 disposed within a target vessel 90. The VAD 80 can define a total VAD length ($L_T$) extending from a proximal end 82 to a distal tip 84. A dwell length ($L_D$) can be a length of the VAD 80 that is disposed within the vessel 90. As will be appreciated, for the VAD 80 to remain engaged with the target vessel 90, a length of the VAD 80 must extend through the insertion site 72 and into the vessel 90. As will be appreciated, various factors can affect the dwell length ($L_D$) for a given VAD 80. These factors can include the total VAD length ($L_T$), the depth ($D_V$) of the target vessel 90 relative to the skin surface 70, and the angle of insertion ($\theta$) of the VAD 80 relative to the skin surface 70. In an embodiment, the insertion angle ($\theta$) can be between 1° and 90° relative to the skin surface 70.

In an embodiment, the VAD selection logic 164 can be configured to retrieve information on the depth ($D_V$) of the target vessel 90 from the vessel selection logic 162, the insertion angle ($\theta$) 214C or range of insertion angles ($\theta$) from the insertion parameters 214 and information on the total VAD length ($L_T$) to determine a dwell length ($L_D$), and determine if the dwell length ($L_D$) is less than a minimum dwell length parameter 214B.

In an embodiment, the VAD selection logic 164 can select a VAD icon 220 that represents a VAD 80 that can access the target vessel 90, while remaining within one or more of the insertion parameters 214. In an embodiment, the VAD selection logic 164 can provide a list of one or more VAD icons 220, each VAD icon 220 of the list of VAD icons can represent a VAD 80 of one or more VAD's that can access the target vessel 90, while remaining within one or more of the insertion parameters 214. In an embodiment, the VAD selection logic 164 can automatically select a VAD icon 220, as described herein, a user can then select a second VAD icon 220B that represents a different VAD with different specifications that can also access the target vessel 90, while remaining within one or more of the insertion parameters 214. Advantageously, the system 100 can automatically select a VAD icon 220 for the user to access the target vessel 90, and provide a VAD with the largest possible gauge (i.e. largest lumen diameter), while remaining within one or more of the insertion parameters 214. Further the user can select a different VAD icon, representing a different VAD device that can also access the target vessel 90, while remaining within one or more of the insertion parameters 214.

With further reference to FIGS. 2A-2B, in an embodiment, the VAD selection logic 164 can provide alerts and/or VAD information 216 directed to the selected VAD icon 220, e.g. the first VAD icon 220A, superimposed on the screen 104, or information about the one or more VAD's that are able to access the target vessel 90. Advantageously, the system 100 can image a subcutaneous portion of the patient, identify a target vessel 90, determine a cross-sectional area or diameter of the vessel 90 and a depth of the vessel relative to the skin surface 70. The system 100 can then determine which VAD 80 can be used to access the vessel 90 while remaining within one or more insertion parameters 214, e.g. the percentage vessel occupancy parameter 214A, and dwell length parameter 214B, based on the specifications of the VAD and an angle, or range of angles, of insertion 214C. As such, the system 100 can advise the clinician on which VAD(s) 80 to use to access the target vessel 90.

In an exemplary method of use, a system 100 is provided, as described herein. A clinician can image a portion of the patient including the target vessel 90 using the probe 106. In an embodiment, the system 100 uses an ultrasound modality to image the patient, however, it will be appreciated that other modalities are also contemplated. An image 202 of the target vessel 90 can be provided on the display 104 and a clinician can manipulate a target vessel selection ring 210 to position and align with a target vessel 90 in the image 202. Optionally, the system 100 can automatically align a vessel selection ring 210 with a target vessel 90 in the image 202. In an embodiment, one or more vessel selection rings 210 can be aligned with one or more target vessels 90 in the image 202. For example, a first vessel selection ring can be aligned with a first target vessel, a second vessel selection ring can be aligned with a second target vessel, etc.

The system 100 can then determine a cross-sectional size and depth of the target vessel 90 based on the size, shape and position of the vessel selection ring 210 within the image 202. The system 100 can retrieve one or more insertion parameters 214 and retrieve information about one or more VAD's 80, either from the data store 152 or from a network or remote database, as described herein. Optionally, the clinician can enter the insertion parameters 214 or the information about one or more VAD's 80 to the system 100 either before or after imaging the target vessel 90. The system 100 can then determine which VAD can access the target vessel 90 while remaining within the insertion parameters 214, as described herein. In an embodiment, the system 100 can automatically select a VAD, represented by a VAD icon 220 that can access the target vessel 90 to provide, for example, the largest gauge VAD or shortest total VAD length (L$_T$), while remaining within the insertion parameters 214. In an embodiment a clinician can select a VAD icon 220 representing a VAD 80. The system 100 can display the icon 220 within the target vessel 90. Further the system 100 can display information to the clinician, including the insertion parameters 214, target vessel information, VAD information, patient information, system information, and the like.

Figure 3:
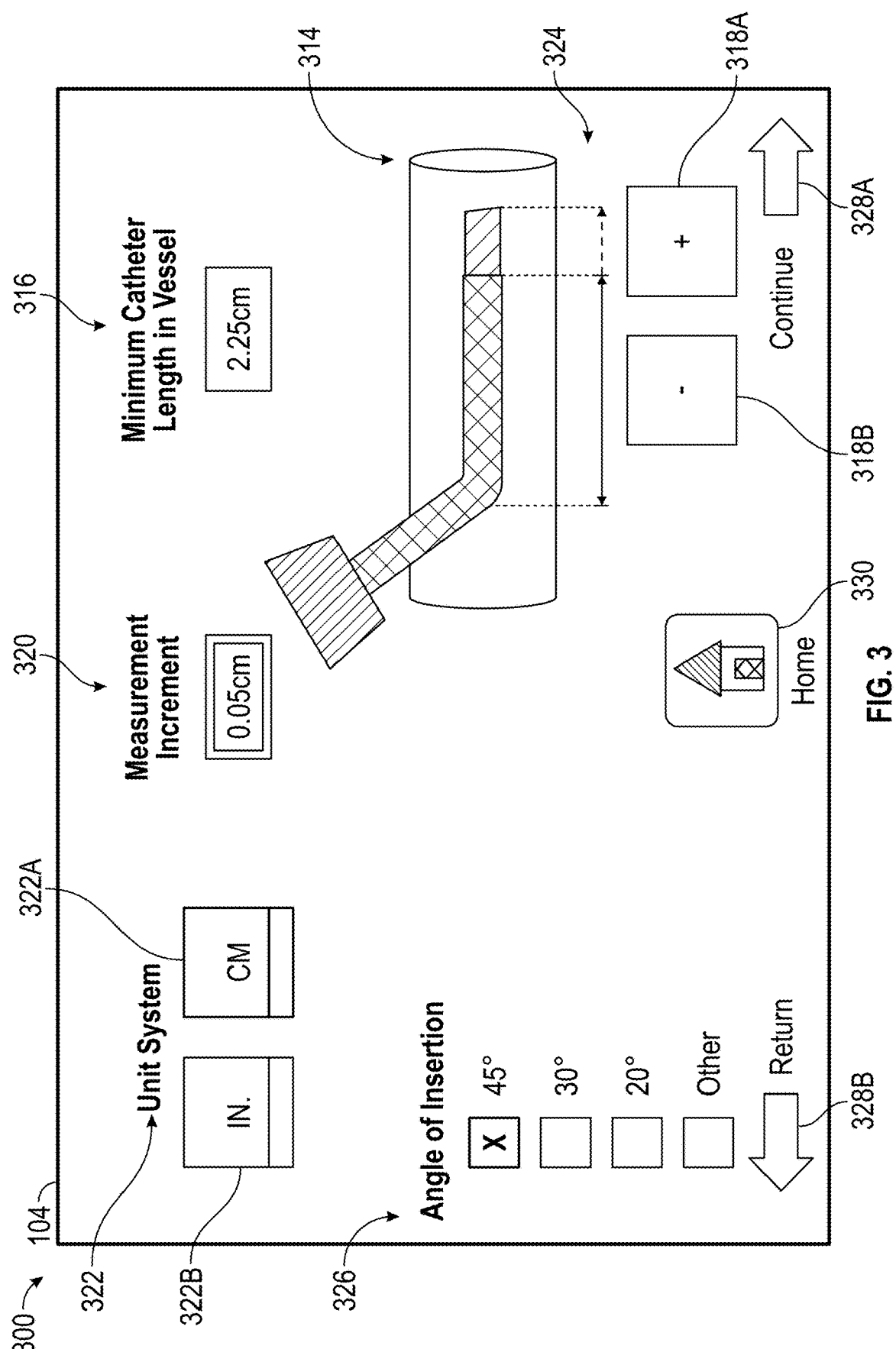
FIG. 3 illustrates a screenshot of a parameter entry screen of the system of FIG. 1A, in accordance with embodiments disclosed herein.

In an embodiment, as shown in FIG. 3, the system 100 can include a parameter input logic 166 configured to provide a parameter input screen 300. The parameter input screen 300 can include a plurality of icons configured to allow a user to modify one or more of the insertion parameters 214. For example, a target vessel icon 314 and/or an indicator icon 316, can correspond to the minimum dwell length parameter 214B. The indicator icon 316 may be configured to be changed to match the minimum dwell length parameter 214B. In an embodiment, the minimum dwell length parameter 214B can be selected by the clinician and entered to the system 100 by way of the parameter input screen 300. In an embodiment, the minimum dwell length parameter 214B can be predetermined by the system 100.

In an embodiment, the clinician can adjust the minimum dwell length parameter 214B. The indicator icon 316 may be configured to be modified incrementally by way of a positive icon 318A or a negative icon 318B. For example, selecting the positive icon 318A can increase the dwell length parameter 214B while selecting the negative icon 318B will decrease the dwell length parameter 214B. The standard unit of measure may be modified by the user by selecting a measurement increment icon 320. The measurement increment icon 320 may be configured to allow the user to change the standard increment of the unit of measure depicted on the display 104. For example, the unit of measure increment may be 0.05 cm. and the user can change the unit of measure increment to be 1.0 cm, 0.1 cm, 0.01 cm. or the like. However, it will be appreciated that greater or lesser increments are also contemplated.

In some embodiments, the parameter input screen 300 includes a unit system icon 322 that allows a user to select between imperial or metric measurement systems of the indicator icon 316. In some embodiments, the user may select the desired units of measure displayed for the indicator icon 316. For example, the indicator icon 316 may be configured to be displayed in metric by selecting the centimeter unit of the unit system icon 322A. However, the user may select the inches unit of the unit system icon 322B which would display the indicator icon 316 in imperial units. In some embodiments, the unit system icon 322 may be configured to change the unit of measurement displayed on all user interfaces on the display 104.

In some embodiments, the icon 314 can further include a catheter dwell length icon 324 indicating, e.g. by an arrow or similar graphical representation, the dwell length of the catheter in the blood vessel. In some embodiments, as the indicator icon 316 is increased or decreased by the positive icon 318A or the negative icon 318B, the catheter dwell length icon 324 may be modified to correspondingly increase or decrease in displayed length.

The parameter input screen 312 may include an angle of insertion (θ) selection panel 326 that includes a selection of predetermined angles of insertion (θ), for example "45°", "30°", "20°" or the like. However, it will be appreciated that other predetermined angles, or predetermined ranges of angles, are also contemplated. In an embodiment, the user can select a specified angle of insertion (θ) by selecting "other" and entering an angle of insertion. Optionally, the angle of insertion (θ) entered by the user may be limited to a predetermined range. As used herein, the angle of insertion (θ) is defined as angle of the catheter relative to a surface of a patient's skin at the point of insertion. In some embodiments, the "other" option may be configured to allow the user to specify the angle of insertion if the angle is not listed on the angle of insertion selection panel 326.

In some embodiments, the parameter input screen 300 includes one or more arrow icons 328A, 328B to help a user navigate through the user interface of the system 110. In some embodiments, the one or more arrow icons 328A, 328B can be indicated by text that includes "continue" or "return". In some embodiments, the parameter input screen 300 may include a home icon 330 configured to return the user to a home screen, navigation page, a displayed ultrasound image screen 200, or the like.

Figure 4:
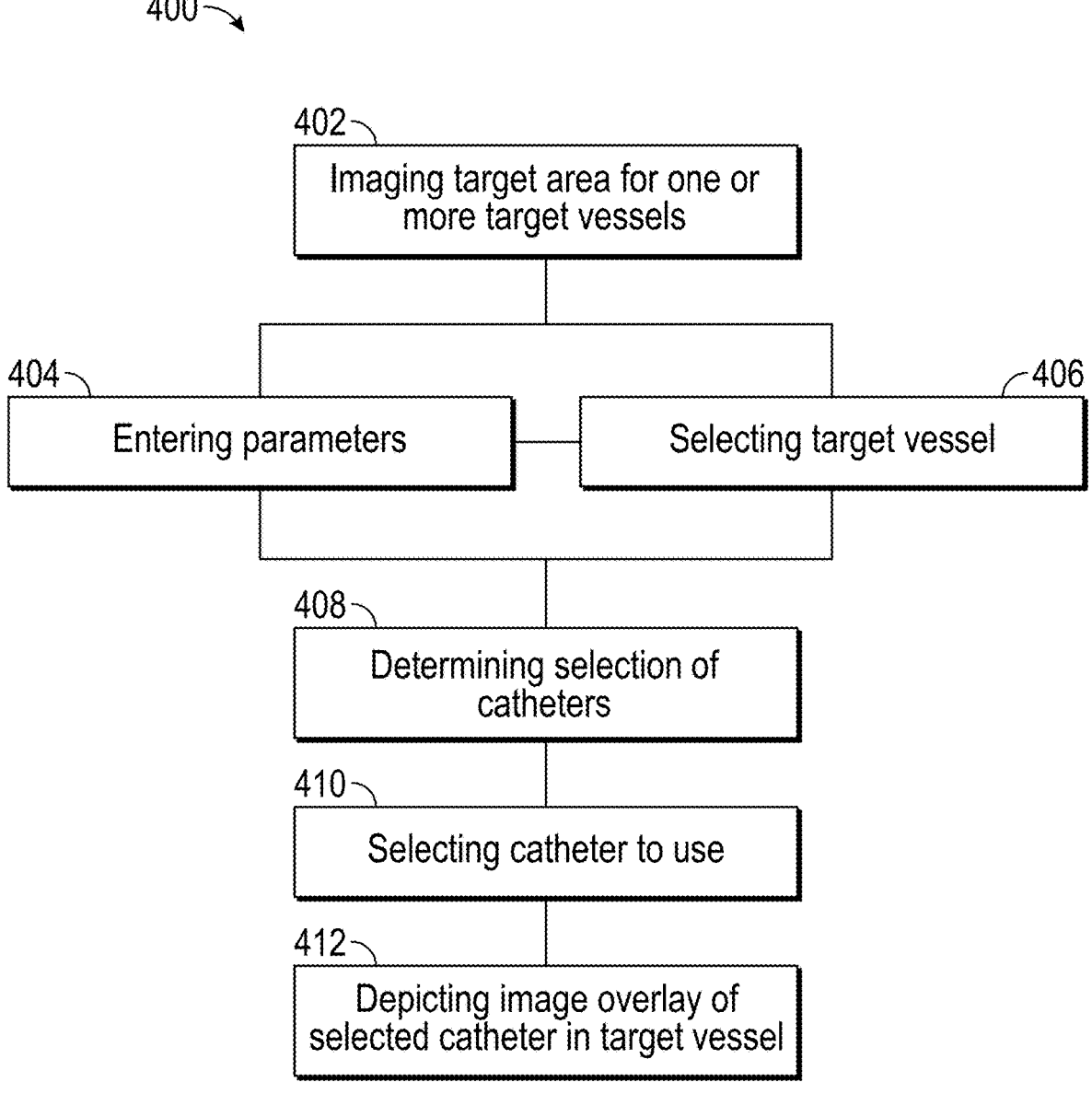
FIG. 4 illustrates a flow chart of a method of use for the system of FIG. 1A, in accordance with embodiments disclosed herein.

FIG. 4 illustrates a block diagram of a method for selecting a vascular access device for accessing a target blood vessel, in accordance with embodiments disclosed herein. The method 400 includes imaging a target area for one or more blood vessels (block 402). In some embodiments, imaging includes using an ultrasound vessel assessment system 100 having a console 102 including a display 104 and communicatively coupled to an ultrasound probe 106, as described herein.

In some embodiments, the system 100 may be configured to receive a user input to define one or more insertion parameters 214 and determine a selection of VAD's 80 that may be capable of accessing a target blood vessel 90. The method 400 further includes entering parameters (block 404), such as the angle of insertion, maximum percentage occupancy, and the minimum dwell length as parameters to use for choosing a catheter. In some embodiments, entering includes entering one or more of the angle of insertion, the maximum percentage occupancy, and the minimum catheter dwell length on a parameter input screen 300.

The method 400 can further include selecting one or more target vessels (block 406). The method 400 includes determining a selection of VAD's 80 (block 408) that are capable of accessing the target vessel 90 based upon one or more insertion parameters 214 such as the angle of insertion, the target vessel depth, the maximum percentage occupancy, and/or the minimum catheter dwell length. The method 400 includes selecting a catheter to use (block 410). In some embodiments, selecting the catheter to use includes selecting from the selection of VAD's 80 generated by the system 100. The method 400 includes depicting an ultrasound image overlay of the selected catheter in a target vessel 90 (block 412). In some embodiments, the user can move between entering parameters (block 404) and selecting one or more target vessels (block 406) until the user is satisfied with the results.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A vessel assessment system, comprising:
an ultrasound probe; and
a console communicatively coupled to the ultrasound probe, the console comprising a display and one or more logic modules coupled to one or both of a processor and a data store, the one or more logic modules comprising:
   an imaging logic configured to provide an image of a target vessel;
   a vessel selection logic configured to determine one or both of a diameter and a cross-sectional area of the target vessel; and
   a vascular access device (VAD) selection logic configured to retrieve an insertion parameter, and automatically select a VAD icon from a list of VAD icons, the VAD icon representing a vascular access device configured to access the target vessel within the insertion parameter.

2. The vessel assessment system according to claim 1, wherein the ultrasound probe is configured to send an acoustic signal and detect a reflected acoustic signal, and the imaging logic is configured to retrieve information from the ultrasound probe and provide the image of the target vessel disposed subcutaneously.

3. The vessel assessment system according to claim 1, wherein the vessel selection logic is configured to retrieve image information from the imaging logic, and automatically align a vessel selection ring, superimposed on the image, with the target vessel.

4. The vessel assessment system according to claim 1, wherein the vessel selection logic is configured to receive an input from a user to manipulate a vessel selection ring, superimposed on the image, to align with the target vessel.

5. The vessel assessment system according to claim 4, wherein the vessel selection ring can change one or more of a diameter and a shape of the vessel selection ring to align the vessel selection ring with the target vessel.

6. The vessel assessment system according to claim 5, wherein the vessel selection ring can change the shape to align the vessel selection ring with the target vessel.

7. The vessel assessment system according to claim 1, wherein the insertion parameter includes one or more of a percentage vessel occupancy parameter, a dwell length parameter, and an insertion angle parameter.

8. The vessel assessment system according to claim 1, wherein the VAD selection logic is further configured to superimpose the VAD icon on the image, and align the VAD icon with the target vessel.

9. The vessel assessment system according to claim 1, wherein a size of the VAD icon is scaled relative to the target vessel to provide a visual comparison of the vascular access device relative to the target vessel.

10. The vessel assessment system according to claim 1, wherein the VAD icon of the list of VAD icons includes a specification measurement of the vascular access device, each VAD icon of the list of VAD icons representing a different vascular access device.

11. A vessel assessment tool, comprising:
a processor; and
memory communicatively coupled to the processor, the memory comprising machine readable instructions that when executed by the processor, cause the processor to execute:
   i) an imaging logic configured to provide an image of a target vessel disposed subcutaneously;
   ii) a vessel selection logic configured to determine one or more of a diameter, a cross-sectional area, and a depth of the target vessel; and
   iii) a vascular access device (VAD) selection logic configured to retrieve information from the vessel selection logic, and retrieve an insertion parameter, and automatically provide a VAD icon representing a vascular access device configured to access the target vessel within the insertion parameter.

12. The vessel assessment tool according to claim 11, further including an ultrasound probe configured to send and receive an acoustic signal, and wherein the imaging logic is configured to retrieve information from the ultrasound probe to provide the image of the target vessel.

13. The vessel assessment tool according to claim 11, wherein the vessel selection logic is further configured to identify one or more features of the image, and automatically align a vessel selection ring, superimposed on the image, with the target vessel.

14. The vessel assessment tool according to claim 11, wherein the vessel selection logic is further configured to receive an input from a user to manipulate a vessel selection ring, superimposed on the image, to align with the target vessel.

15. The vessel assessment tool according to claim 14, wherein the vessel selection logic is configured to change one or more of a position, a diameter, an area, and a shape of the vessel selection ring, to align the vessel selection ring with the target vessel.

16. The vessel assessment tool according to claim 15, wherein the vessel selection logic is configured to change the shape of the vessel selection ring, to align the vessel selection ring with the target vessel.

17. The vessel assessment tool according to claim 11, wherein the VAD icon is superimposed on the image, and aligned with the target vessel.

18. The vessel assessment tool according to claim 11, wherein a size of the VAD icon is scaled relative to the image to provide a visual comparison of the vascular access device relative to the target vessel.

19. The vessel assessment tool according to claim 11, wherein the VAD selection logic provides a list of one or more VAD icons, each VAD icon of the list of one or more VAD icons representing a different vascular access device.

20. The vessel assessment tool according to claim 19, wherein the VAD selection logic is configured to receive an input to select a second VAD icon from the list of one or more VAD icons, representing a second vascular access device.

21. A method of selecting a vascular access device for accessing a target vessel, comprising:

detecting a reflected ultrasonic acoustic signal using an ultrasonic imaging device;
    providing an image of the target vessel disposed subcutaneously;
    determining one or more of a depth, a diameter, and a cross-sectional area of the target vessel;
    retrieving an insertion parameter including one or more of a maximum percentage vessel occupancy parameter, a minimum dwell length parameter, and an insertion angle parameter; and automatically selecting, by a vascular access device (VAD) selection logic, the vascular access device, a diameter of the vascular access device being equal to or less than the maximum percentage vessel occupancy parameter, or a dwell length metric of the vascular access device being equal to or greater than the minimum dwell length parameter.

22. The method according to claim 21, further including the VAD selection logic automatically aligning a vessel selection ring, superimposed on the image, with the target vessel.

23. The method according to claim 21, further including providing an input to the VAD selection logic to modify a vessel selection ring, superimposed on the image, to align the vessel selection ring with the target vessel.

24. The method according to claim 23, wherein modifying the vessel selection ring includes changing a shape of the vessel selection ring.

25. The method according to claim 21, further including retrieving the insertion angle parameter, the depth of the target vessel and a total length of the vascular access device and determining the dwell length metric of the vascular access device.

26. The method according to claim 21, further including superimposing a VAD icon on the image of the target vessel, the VAD icon representing one or both of the diameter and a cross-sectional area of the vascular access device relative to the target vessel.

27. The method according to claim 21, further including selecting, by a user interface, a second VAD icon representing a second vascular access device, a diameter of the second vascular access device being less than the maximum percentage vessel occupancy parameter, or a dwell length metric of the second vascular access device being greater than the minimum dwell length parameter.

* * * * *